United States Patent
Crison et al.

(10) Patent No.: US 6,669,954 B2
(45) Date of Patent: Dec. 30, 2003

(54) CONTROLLED RELEASE OF DRUGS

(76) Inventors: John R. Crison, 272 Highlake Ave., Ann Arbor, MI (US) 48103; Gordon L. Amidon, 2079 S. Seventh St., Ann Arbor, MI (US) 48103

( * ) Notice: Subject to any disclaimer, the term of this patent is extended or adjusted under 35 U.S.C. 154(b) by 0 days.

(21) Appl. No.: 09/768,852

(22) Filed: Jan. 24, 2001

(65) Prior Publication Data

US 2002/0004067 A1 Jan. 10, 2002

Related U.S. Application Data (60) Provisional application No. 60/177,822, filed on Jan. 25, 2000.

(51) Int. Cl.$^7$ .................................................. A61K 9/22
(52) U.S. Cl. ........................ 424/456; 424/472; 424/453; 424/464; 424/466; 424/468; 424/470
(58) Field of Search ............................... 424/472, 453, 424/464, 466, 468, 470, 456

(56) References Cited

U.S. PATENT DOCUMENTS

| | | | |
|---|---|---|---|
| 4,327,725 A | 5/1982 | Cortese et al. | 128/260 |
| 4,361,546 A | 11/1982 | Stricker et al. | 424/19 |
| 4,439,196 A | 3/1984 | Higuchi | 604/890 |
| 4,475,916 A | 10/1984 | Himmelstein | 604/890 |
| 4,595,583 A | 6/1986 | Eckenhoff et al. | 424/15 |
| 4,608,048 A | 8/1986 | Cortese et al. | 604/890 |
| 4,609,374 A | 9/1986 | Ayer | 604/892 |
| 4,627,850 A | 12/1986 | Deters et al. | 604/892 |
| 4,642,233 A | 2/1987 | Urquhart et al. | 424/19 |
| 4,670,287 A | 6/1987 | Tsuji | 427/3 |
| 4,723,958 A | 2/1988 | Pope et al. | 604/890.1 |
| 4,773,907 A | 9/1988 | Urquhart et al. | 424/467 |
| 4,777,049 A | 10/1988 | Magruder et al. | 424/457 |
| 4,786,500 A | 11/1988 | Wong | 424/422 |
| 4,814,181 A | 3/1989 | Jordan et al. | 424/892 |
| 4,816,259 A | 3/1989 | Matthews et al. | 424/463 |
| 4,874,388 A | 10/1989 | Wong et al. | 604/891.1 |
| 4,927,632 A | 5/1990 | Wong | 424/422 |
| 5,011,692 A | 4/1991 | Fujioka et al. | 424/426 |
| 5,017,381 A | 5/1991 | Maruyama et al. | 424/472 |
| 5,045,082 A | 9/1991 | Ayer et al. | 604/892.1 |
| 5,074,857 A | 12/1991 | Shepherd et al. | 604/891.1 |
| 5,110,597 A | 5/1992 | Wong et al. | 424/438 |
| 5,141,752 A | 8/1992 | Ayer et al. | 424/473 |
| 5,178,867 A | 1/1993 | Guittard et al. | 424/473 |
| 5,209,746 A | 5/1993 | Balaban et al. | 604/892.1 |
| 5,221,278 A | 6/1993 | Linkwitz et al. | 604/890.1 |
| 5,223,265 A | 6/1993 | Wong | 424/473 |
| 5,232,705 A | 8/1993 | Wong et al. | 424/473 |
| 5,260,068 A | 11/1993 | Chen | 424/451 |
| 5,260,069 A | 11/1993 | Chen | 424/451 |
| 5,312,388 A | 5/1994 | Wong et al. | 604/892.1 |
| 5,312,390 A | 5/1994 | Wong | 604/892.1 |
| 5,340,590 A | 8/1994 | Wong et al. | 424/473 |
| 5,342,624 A | 8/1994 | McNeill et al. | 424/451 |
| 5,387,421 A * | 2/1995 | Amidon et al. | 424/472 |
| 5,429,822 A | 7/1995 | Gresser et al. | 424/426 |
| 5,443,459 A | 8/1995 | Wong et al. | 604/892.1 |
| 5,472,708 A | 12/1995 | Chen | 424/451 |
| 5,474,784 A | 12/1995 | Stevens et al. | 424/456 |
| 5,474,786 A | 12/1995 | Kotwal et al. | 424/472 |
| 5,498,255 A | 3/1996 | Wong | 604/892.1 |
| 5,508,040 A | 4/1996 | Chen | 424/451 |
| 5,516,527 A | 5/1996 | Curatolo | 424/461 |
| 5,531,736 A | 7/1996 | Wong et al. | 604/892.1 |
| 5,650,170 A | 7/1997 | Wright et al. | 424/473 |
| 5,770,224 A | 6/1998 | Rashid et al. | 424/472 |
| 5,795,588 A | 8/1998 | Sauter | 424/451 |
| 5,800,422 A | 9/1998 | Dong et al. | 604/892.1 |
| 5,897,874 A | 4/1999 | Stevens et al. | 424/451 |

* cited by examiner

Primary Examiner—Thurman K. Page
Assistant Examiner—Rachel M. Bennett
(74) Attorney, Agent, or Firm—Gifford, Krass, Groh, Sprinkle, Anderson & Citkowski, P.C.

(57) ABSTRACT

A device for controlled release of pharmaceutical agents and a method for use of the device. The drug delivery device comprises a covered container with an aperture and an aperture cover, containing a pharmaceutical agent and an excipient formulation.

43 Claims, 7 Drawing Sheets

FIG - 1
PRIOR ART $$\frac{dm}{dt} = SA \cdot \frac{D_{eff}}{\delta}(C_s - C_b)$$

CONTROLLED RELEASE OF DRUGS

RELATED APPLICATION

This application claims priority of U.S. Provisional Patent Application 60/177,822 filed Jan. 25, 2000 and is incorporated herein by reference.

BACKGROUND OF THE INVENTION

1. Field of the Invention

The invention relates generally to drug delivery systems, more specifically, the invention relates to a device and a method for controlling release of pharmaceutical agents.

2. Description of the Related Art

The advantages of controlled release preparations of therapeutic agents are well-established. When a drug release is non-controlled, the concentration of drug available in the bloodstream after administration quickly rises and then declines. It is desirable to maintain more constant drug levels over time, allowing administration of fewer doses per day, making patient compliance more likely and reducing the frequency of swings of drug levels in the patient's system. Controlled release preparations are an important means of avoiding an excessively rapid increase in drug concentration and attendant side-effects. In addition, such preparations prevent the drug concentration from falling below therapeutic levels.

Figure 1:
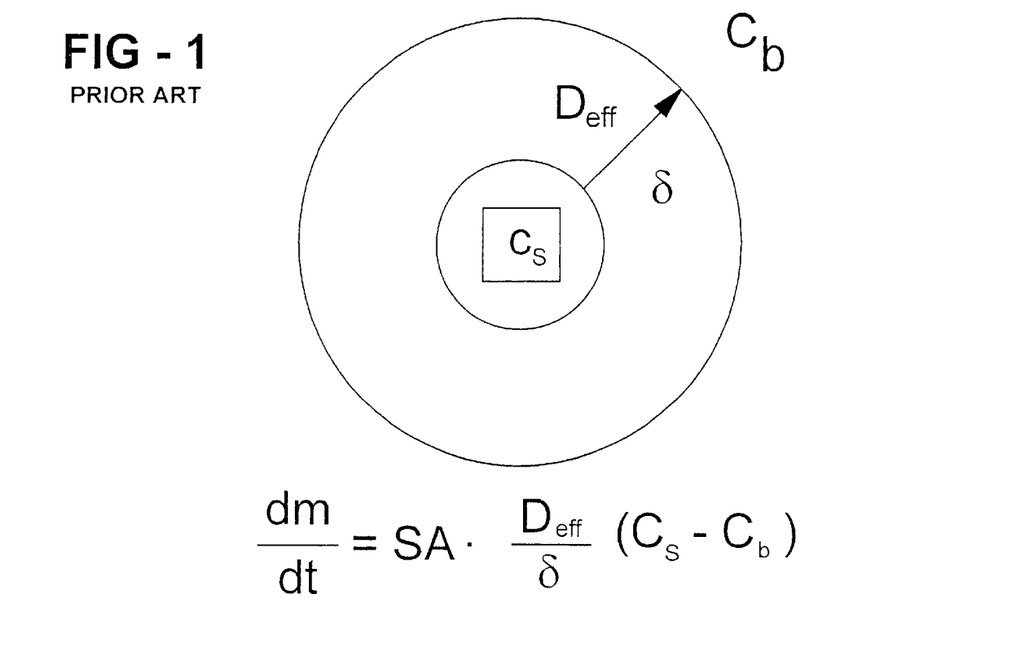
FIG. 1 is a drawing from the prior art illustrating the mathematical relationship between effective diffusivity, drug solubility and the thickness of the diffusional boundary layer.

The fundamental parameters that affect the release of drug from a controlled release dosage form include the solubility of the drug, Cs, the effective diffusivity of the drug, $D_{eff}$, and the surface area available for release of the drug from the dosage form, SA. FIG. 1 illustrates the relationship between these factors where m is mass, t is time, $D_{eff}$ is the effective diffusivity, SA is the surface area, Cs is the concentration of drug in solution at the surface of the solid, Cb is the concentration of drug in solution in the bulk, and δ is the thickness of the diffusional boundary layer. While there are numerous adaptations on this theory, such as, osmotic controlled release, polymeric barriers, encapsulation, Cs, $D_{eff}$ and SA remain the rate limiting parameters.

Figure 2:
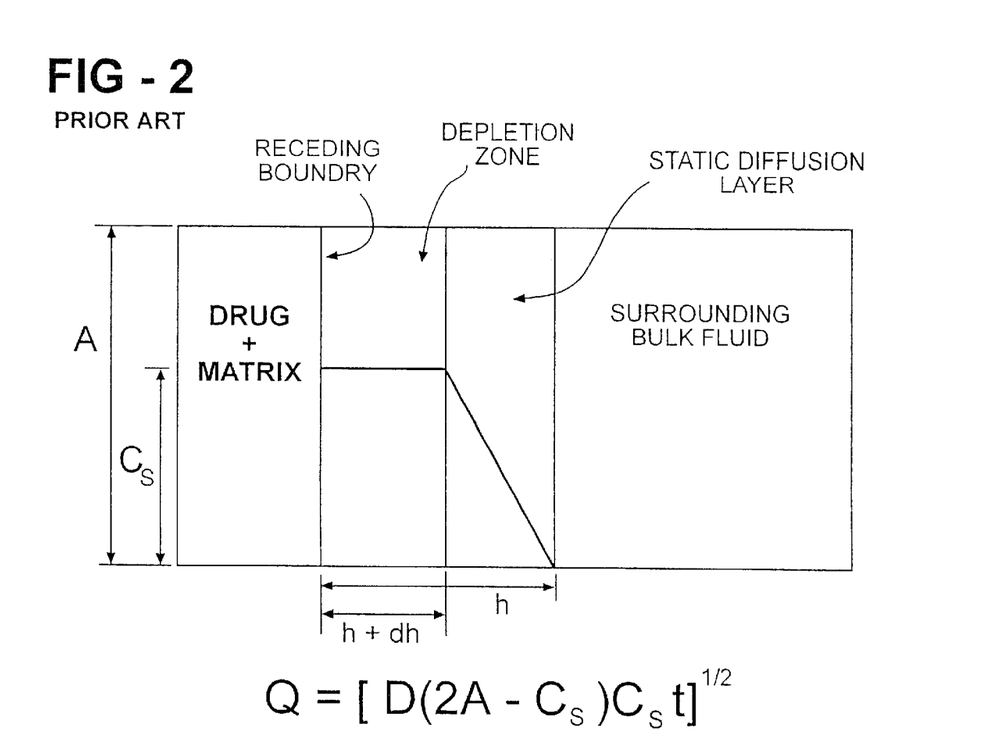
FIG. 2 is a drawing from the prior art illustrating drug release from a matrix and the mathematical relationship between factors affecting release.

In addition to the above analysis, drug release can be controlled using polymeric barriers such as hydrogels. As the hydrogel swells and drug is released, the diffusional boundary layer increases, slowing down the rate of release. FIG. 2 illustrates this process, where Q is the amount of drug release per unit surface area, D is the diffusivity, A is the total amount of drug loaded into the dosage for, Cs is the solubility of the drug and t is the time. Equation 2 is often referred to as the Higuchi equation and is used to estimate the amount of drug that will be released from a matrix delivery system. T. Higuchi, *J. Soc. Cosm. Chem.* 11 (1960) p. 85.

There exists a continuing unmet need for a device and method for controlled delivery which provides simple, inexpensive means of defining release parameters of both water soluble and insoluble pharmaceutically active agents. The present invention controls the release of drug by limiting the surface area available for release and by controlling the length of the diffusion boundary layer.

SUMMARY OF THE INVENTION

The invention provides a device for the controlled release of pharmaceutical agents which includes a coated, apertured container permeable to water that is only semi-permeable to a pharmaceutical agent in the container, a removable aperture cover and an excipient formulation in the container. The invention is also directed to a drug delivery system where the container composition optionally includes a biocompatible polymer. The container may optionally be a hard gelatin capsule. The excipient formulation may include release control components, filling agents and lubricating agents. The drug delivery device may be used to deliver organic, inorganic or organometallic pharmaceutical agents. The container is coated with a covering permeable to water but only semi-permeable to the pharmaceutical agent in the container. The covering may optionally include cellulose acetate. Also provided is a process for drug delivery using the device described.

DETAILED DESCRIPTION OF THE INVENTION

Method of the Present Invention

The present invention provides a device for controlled release of pharmaceutical agents. Release is controlled by defining five parameters: (1) surface area available for release, (2) the rate of drug and excipient hydration and solubility, (3) regulation of the distance the pharmaceutical agent must diffuse through a drug/excipient matrix, (4) diffusion characteristics of the drug/excipient boundary layer and (5) time of removal of a cover from a container aperture.

Definition of Surface Area Available for Release

Figure 3:
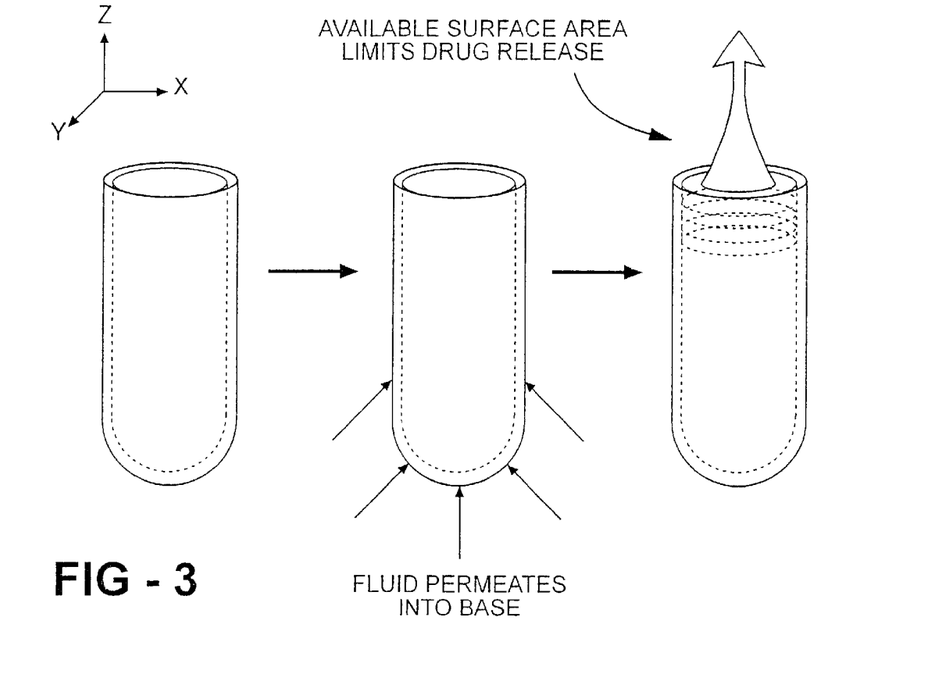
FIG. 3 is a drawing illustrating factors affecting drug release.
Figure 4:
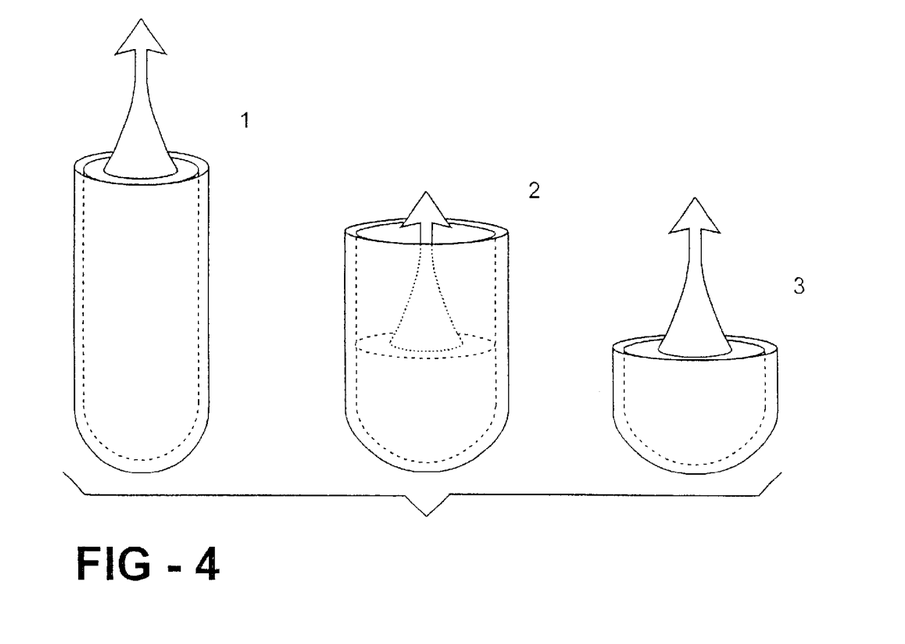
FIG. 4 is a drawing illustrating factors affecting drug release.
Figure 5:
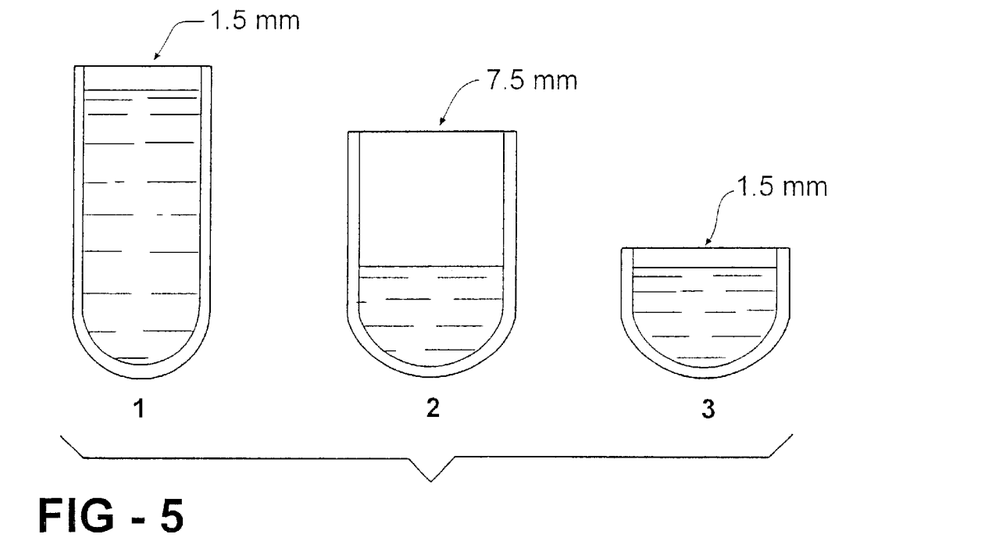
FIG. 5 is a drawing illustrating various formulations of the present invention.

The surface area available for release is defined by at least one opening in the container of the present invention. In a preferred embodiment, the surface area available for release is defined by the choice of the size of the container used. For example, when a relatively small surface area is desired, a No. 3 capsule is chosen, whereas a No. 0 capsule is chosen when a relatively large surface area is desired. FIGS. 3, 4 and 5 show the effects of available surface area on release.

Definition of the Rate of Hydration and Solubility

Release is further controlled by defining the rate of hydration and solubility of the pharmaceutical agent and excipient formulation. Hydration is controlled by defining the permeability of the container and the container cover. The permeability of cellulose acetate, an exemplary container and/or cover material, has a water permeability about an order of magnitude greater than that for salts.

Containers of the Present Invention

The wall of the container of the present invention is permeable to water but semi-permeable to the pharmaceutical agent in the container. "Semi-permeable" as used herein is intended to mean a permeability of less than the permeability relative to water. The rate at which water passes through the container wall depends on the pore size of the container material and the wall thickness. Container material and wall thickness are varied to increase or decrease permeability and will depending on the application. A container suitable for the present invention will maintain its physical and chemical integrity in the environment where the drug is to be delivered for a time sufficient for the drug to be delivered. A container according to the present invention is constructed of a soluble material, illustratively including gelatin, hydroxypropylmethylcellulose; a non-water soluble, semi-permeable to pharmaceutical agent material, illustratively including cellulose acetate; a non-water soluble, non-permeable material; or composites thereof. Any such material suitable for pharmaceutical formation delivery. These illustratively include hard gelatin typically by a water content of about 13% by weight; soft gelatin that is pliable relative to hard gelatin and contains water and other plasticizers; hydroxypropylmethylcellulose; and starch. The preferred environment where the drug is to be delivered is the digestive tract but alternatively is the urinary tract, anal, vaginal, oral or nasal cavities. The environment where the drug is to be delivered will depend on the route of administration as detailed further below. In a preferred embodiment of the present invention the container is a hard gelatin capsule. It will be recognized by those skilled in the art that the container may be composed of any biocompatible material, including synthetic and naturally occurring polymers.

It will be recognized by those skilled in the art that the shape and size of the container of the present invention may be varied. In a preferred embodiment the container may be a gelatin capsule shortened compared to a standard size gelatin capsule.

Container Cover

The rate at which water passes through the container cover depends on the pore size of the cover material and the cover thickness. A container cover according to the present invention is constructed of a soluble material, illustratively including gelatin, hydroxypropylmethylcellulose; a non-water soluble, semi-permeable to pharmaceutical agent material, illustratively including cellulose acetate; a non-water soluble, non-permeable material; or composites thereof. Any such material suitable for pharmaceutical formation delivery. These illustratively include hard gelatin typically by a water content of about 13% by weight; soft gelatin that is pliable relative to hard gelatin and contains water and other plasticizers; hydroxypropylmethylcellulose; and starch. In a preferred embodiment, the covering is a semi-permeable polymer film. A covering according to the present invention illustratively includes cellulose acetate, cellulose acetate butyrate, polyurethane, and other cellulose derivatives. The permeability of the covering is changed as desired for a particular use. For example, the thickness of the covering is varied by application of multiple layers, by dilution of a coating solution before application or by other methods known to those skilled in the art. Technical Bulletin 101, Citric Acid Esters; Technical Bulletin 102, Citrate Plasticizers for Pharmaceutical Coatings; Technical Bulletins 102-1 through 102-5, Pharmaceutical Coatings; Morflex, Inc., 2110 High Point Rd., Greensboro, N.C. (1998). Film Properties of Cellulose Esters, Technical Services & Development, Pharmaceutical Excipients Laboratory, Eastman Chemical Company, Kingsport, Tenn. 37662 (1996). Cellulose Acetate Butyrate, CAB-381-2 and CAB-381-20, Publication No. E-186A, Eastman Coating Chemicals, Kingsport, Tenn. 37662. J. Yuan, S. Wu, A Feasibility Study Using Cellulose Acetate and Cellulose Acetate Butyrate, Pharm. Tech., p. 92–106 (October 2000). In addition, either the inner surface, the outer surface, or both surfaces, of the container may be coated by the covering. The covering ma also coat the aperture cover if desired.

Regulation of the Diffusion Distance

It is an aspect of the present invention that release of the pharmaceutical agent is controlled in part by defining the distance through which the pharmaceutical agent must diffuse to exit the container. The delivery device of the present invention is configured such that the pharmaceutical agent cannot diffuse through the wall of the container. Therefore the release takes place through the aperture of the container. The distance that the pharmaceutical agent must travel to reach the aperture is defined by the size of the container and the location of the pharmaceutical agent within the container. FIGS. 4 and 5 illustrate selected container/content configurations where both diffusion distance and surface area are varied to obtain a desired rate of release.

Regulation of Diffusivity

It is an aspect of the present invention that release is controlled by the size and composition of the diffusional boundary layer. The diffusional boundary layer is composed of excipients which regulate the diffusivity of pharmaceutical agents. The diffusional boundary layer is formed when the container is exposed to a water-containing environment. Water enters the container, hydrating the pharmaceutical agent and excipients contained therein resulting in the formation of the diffusional boundary layer. Diffusivity of pharmaceutical agents through the diffusional boundary layer may be regulated by definition of the porosity of the layer, definition of the fluidity of the layer, definition of the polarity of the layer and definition of the molecular composition of the layer. The diffusional boundary layer is formulated such that it remains with the container for a period of time sufficient to allow drug delivery to the desired location.

Composition of the Diffusional Boundary Layer

It is an aspect of the present invention that release is controlled by the composition of the diffusional boundary layer. The diffusional boundary layer comprises an excipient formulation and the pharmaceutical agents. The excipient formulation may contain release control components, fillers, binders, lubricants. In a preferred embodiment, a hydroxyalkylcellulose may be used alone or in combination with carbomer as release control components in the drug delivery system of the present invention. Further illustrative examples of release control components include: alpha-starch, gum arabic, hydroxypropylcellulose, carboxymethylcellulose, polyvinylpyrrolidone, acrylic copolymers such as acrylate/alkylacrylate copolymers, polyacrylamides, polysaccharides, hydroxypropylmethylcellulose, natural gums and clays, and, as lipophilic gelling agents, representative thereof are the modified clays such as bentones, fatty acid metal salts such as aluminum stearates, hydrophobic silica, hydroxypropylmethyl cellulose, sodium carboxymethyl cellulose, hydroxyethyl cellulose, polyethylenes and ethylcellulose and a PEG of appropriate molecular weight.

In a preferred embodiment, a filler in the excipient formulation of the present invention is a saccharide. Further examples of fillers which may be used in the present invention illustratively include lactose, starches, saccharides, sucrose, glucose, mannitol, and silicic acid.

In a preferred embodiment, magnesium stearate is a lubricant in the present invention. Further examples of lubricants which may be used in the present invention illustratively include talc, calcium stearate, solid polyethylene glycols, sodium lauryl sulfate, or mixtures thereof.

The excipient formulation may further contain inert customary ingredients or carriers such as sodium citrate or dicalcium phosphate and (a) binders, as for example, carboxymethylcellulose, alignates, gelatin, polyvinylpyrrolidone, sucrose, and acacia, (b) humectants, as for example, glycerol, (c) disintegrating agents, as for example, agar—agar, calcium carbonate, potato or tapioca starch, alginic acid, certain complex silicates, and sodium carbonate, (d) solution retarders, as for example paraffin, (e) absorption accelerators, as for example, quaternary ammonium compounds, (f) wetting agents, as for example, cetyl alcohol, and glycerol monostearate and (g) adsorbents, as for example, kaolin and bentonite.

Besides such inert diluents, the excipient formulation can also include adjuvants, such as emulsifying and suspending agents, sweetening, flavoring, and perfuming agents.

It will be apparent to those skilled in the art that components of the excipient formulations may have multiple functions in the drug delivery device of the present invention. For example, an ingredient listed above as a filler, such as lactose, may also function as a release control component.

Depending on the desired release characteristics, the excipient formulation may be mixed with the pharmaceutical agent to be delivered. Alternatively, the excipient formulation and the pharmaceutical agent may be placed in the container in a two or more layers.

The excipient formulation may be swellable on hydration to further regulate the size of the diffusion boundary layer.

Aperture Cover

The aperture cover remains in place while the boundary layer is forming in the container. Once the boundary layer is formed, the aperture cover is removable to expose the surface area available for release of a pharmaceutical agent. The aperture cover may be a cap for a gelatin capsule or a film. The cover may also be an integral part of the container comprising a different wall composition formulated so that it does not retain its physical and chemical integrity in the location where drug delivery is desired. The aperture cover may be removed by dissolution, by digestion and by osmotic pressure. It will be appreciated that other means for aperture cover removal will be clear to those skilled in the art. The timing of the removal of the aperture cover may be preselected by using a material in the manufacture of the aperture cover appropriate to removal according to the environment where the pharmaceutical agent is to be delivered by the drug delivery device.

Preparation of the of the Drug Delivery Device

The present invention is manufactured by 1) coating a hard gelatin capsule with a semi-permeable polymer film such as cellulose acetate, and 2) filling the base with a swellable formulation that when hydrated, remains with the non-dissolving capsule for a specified period of time. Optionally, these steps are performed in reverse order.

Pharmaceutical Agents

The pharmaceutical agents that can be delivered by the present invention include organic, inorganic and organometallic compounds without limitation. The compounds may be water soluble or water insoluble. Further, pharmaceutical agents include beneficial agents that affect a cell, tissue, organ or body system, the body system illustratively including the nervous system, cardiovascular system, immune system, reproductive system, musculoskeletal system, lymphatic system, alimentary system, excretory system, endocrine system, hormone system and blood circulatory system.

Further, pharmaceutical agents which can be included in the drug delivery system of the present invention illustratively include: an analgesic, an anesthetic, an anthelminthic, an antiallergic, an antiarrhythmic, an anti-asthmatic, an antibiotic, an anticonvulsant, an antidepressant, an antidiabetic, an antifungal, an antihypertensive, an antiinflammatory agent, anti-migraine, an antineoplastic, an antiparasitic, an antitumor agent, an anti-ulcer agent, an antiviral, an anxiolytic, a bronchodilator, a cough or cold agent, a cytostatic, a hypnotic, a hypoglycemic, a metastasis inhibitor, a muscle relaxant, a neoplastic, a sedative and a tranquilizer compound. Remington's Pharmaceutical Sciences, 16th Ed., 1980, Mack Publishing Co., Easton, Pa. and in Goodman and Gilman's The Pharmacological Basis of Therapeutics by Hardman and Limbird, 9th Ed., 1996, McGraw-Hill, N.Y. and in The Merck Index: an encyclopedia of chemicals, drugs, and biologicals, 12th Edition, 1996, Merck & Co., Whitehouse Station, N.J.

Pharmaceutical agents deliverable by the present invention are those with a molecular weight in the range from about 50 daltons to about 10,000,000 daltons.

Prodrugs are included in the drug delivery device of the present invention as pharmaceutical agents. The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, it is intended that the present invention include compounds made either using standard organic synthetic techniques, including combinatorial chemistry or by biological methods, such as through metabolism.

The compositions optionally include an effective amount of the selected pharmaceutical agent in combination with a pharmaceutically acceptable carrier and, in addition, may include other medicinal agents, pharmaceutical agents, carriers, or diluents. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

A single pharmaceutical agent is delivered by the drug delivery device of the present invention. Optionally, two or more pharmaceutical agents may be delivered simultaneously by the drug delivery device of the present invention.

In a preferred embodiment of the present invention, pseudoephedrine, nifedipine, acetaminophen or glipizide is a pharmaceutical agent to be delivered.

The exact amount of pharmaceutical agent administered will vary from subject to subject, depending on the age, weight and general condition of the subject, the severity of the disease that is being treated, the location and size of the tumor, the particular compounds used, and the like. An appropriate amount may be determined by one of ordinary skill in the art using only routine experimentation given the teachings herein.

Methods of Administration

The drug delivery system is preferably administered orally but may alternatively be administered to patients, rectally; parenterally such as intravenously, intramuscularly, or subcutaneously; intracisternally; intravaginally; intraperitonally; intravesically; intraventricularly; intracranially; or intrathecally.

An individual to be treated using the drug delivery device of the present invention may be a human or a non-human animal. Illustrative examples of non-human animals that may be treated by administration of pharmaceutical agents using the drug delivery device of the present invention include: sheep, cattle, horses, goats, pigs, chickens, dogs and cats.

EXAMPLES

Example 1

Acetominophen (APAP)

Drug Formulation

An APAP/Carbopol 971P formulation is compressed into cylindrical tablets, each weighing 0.28 grams. The punch and dies used to compress the powder are flat on one end and concave on the other so that the tablet fit into the capsule base for sizes #2 and #0 capsules. Each tablet is compressed using a Carver press at equal pressure per unit surface area.

Capsule Coating

Capsules are coated with cellulose acetate by dipping the capsule bases into a 9% w/w solution of cellulose acetate in acetone with 1.4% w/w triacetin (plasticizer). Two coats are applied to the capsules allowing each coat to dry in between applications.

Formulations Tested

Three different formulations are prepared:

1. Full length size #2 capsule with compressed #2 tablet.
2. Full length size #0 capsule with compressed #0 tablet.
3. Shortened size #0 capsule with compressed #0 tablet.

As shown in FIG. 5, the edge length between the tablet top and the capsule top of Formulation 1 and Formulation 3 are kept the same. The distance from the surface of the tablet to the capsule edge for Formulation 2 is 7.5 mm as compared to 1.5 mm for both Formulations 1 and 3. The surface area available for drug release of Formulations 2 and 3 is 1.5 times that of Formulation 1, while the surface areas available for drug release of Formulations 2 and 3 are equal to each other.

Dissolution Experiments and Analysis

Dissolution experiments are performed using a Vankel USP dissolution apparatus maintained at 37° C. and a paddle speed of 100 rpm. The dissolution medium used is Simulated Intestinal Fluid without Enzymes, USP, pH 7.5. Drug concentrations are determined using a Shimadzu UV160U spectrophotometer. Samples are read at 243.4 nm. Table 1 shows the initial release rates of the 3 formulations and compares the coated preparations with uncoated preparations.

TABLE 1

Initial release rates of the 3 formulations.

| Formulation | Initial Release Rate |
|---|---|
| uncoated (both #2 and #0) | 10.2 mg/hour |
| Formulation #1 | 2.4 mg/hour |
| Formulation #2 | 1.8 mg/hour |
| Formulation #3 | 2.9 mg/hour |

Figure 6:
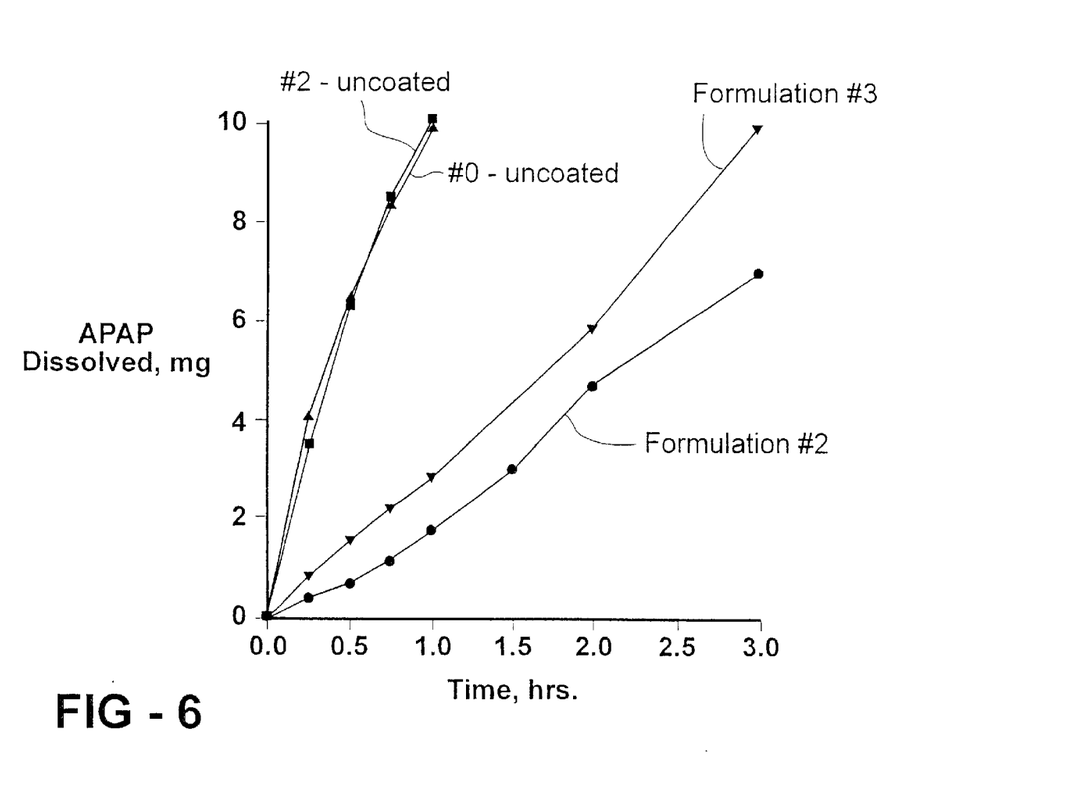
FIG. 6 is a graph illustrating release characteristics of the present invention.
Figure 7:
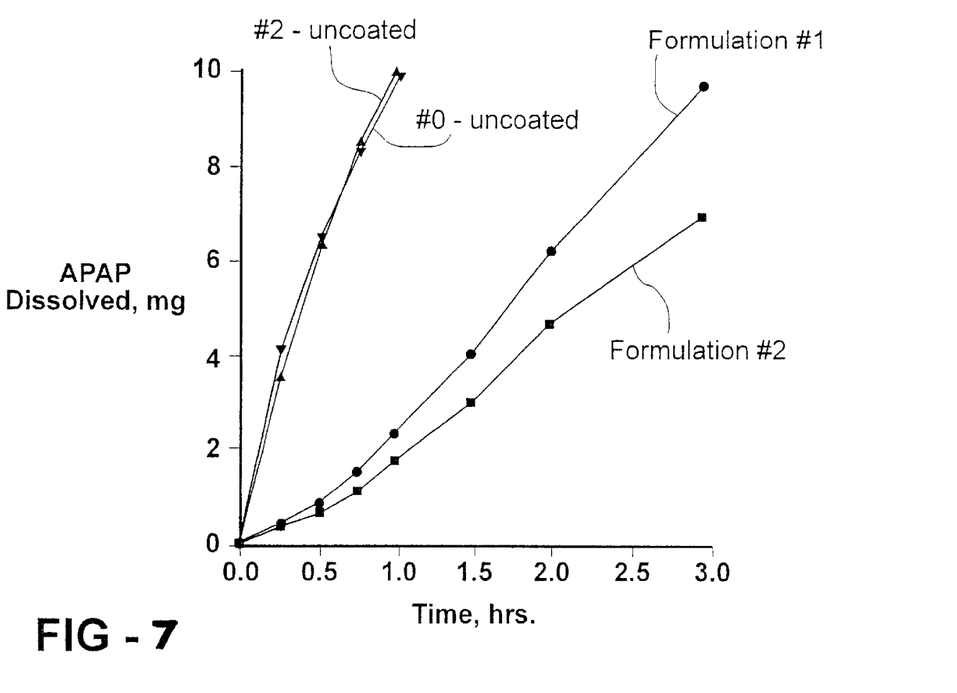
FIG. 7 is a graph illustrating release characteristics of the present invention.
Figure 8:
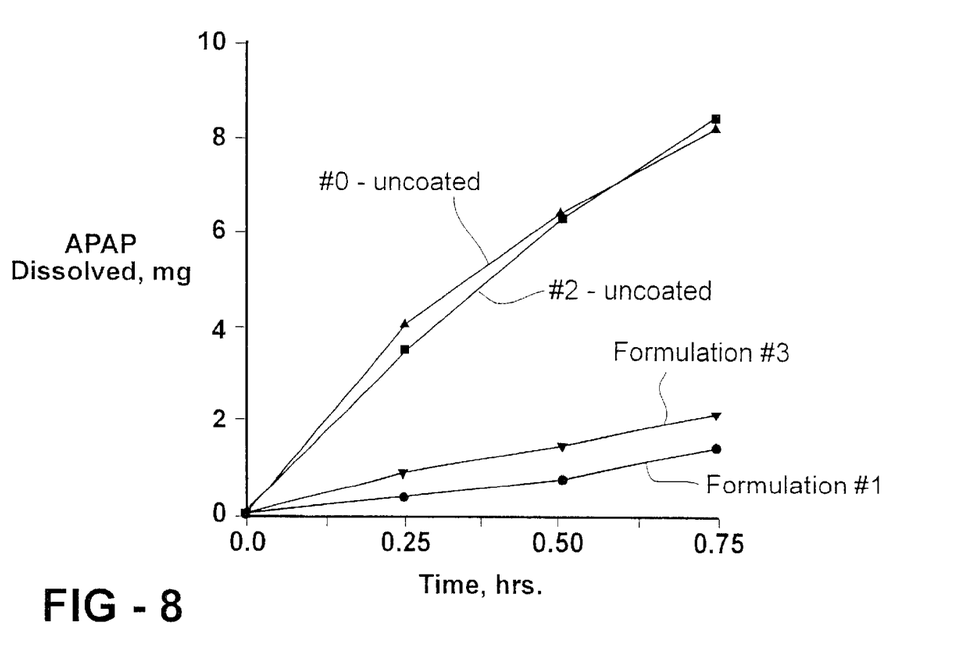
FIG. 8 is a graph illustrating release characteristics of the present invention.

FIGS. 6, 7 and 8 show the release of APAP from formulations 1, 2 and 3.

Differences in release rates among the three formulations correspond with the available surface area (FIG. 8) and the length of the diffusional boundary layer (FIG. 6). Release rates from the non-coated capsules are greater than the non-coated capsules, at least 5 fold.

Example 2

Pseudoephedrine HCl

Figure 9:
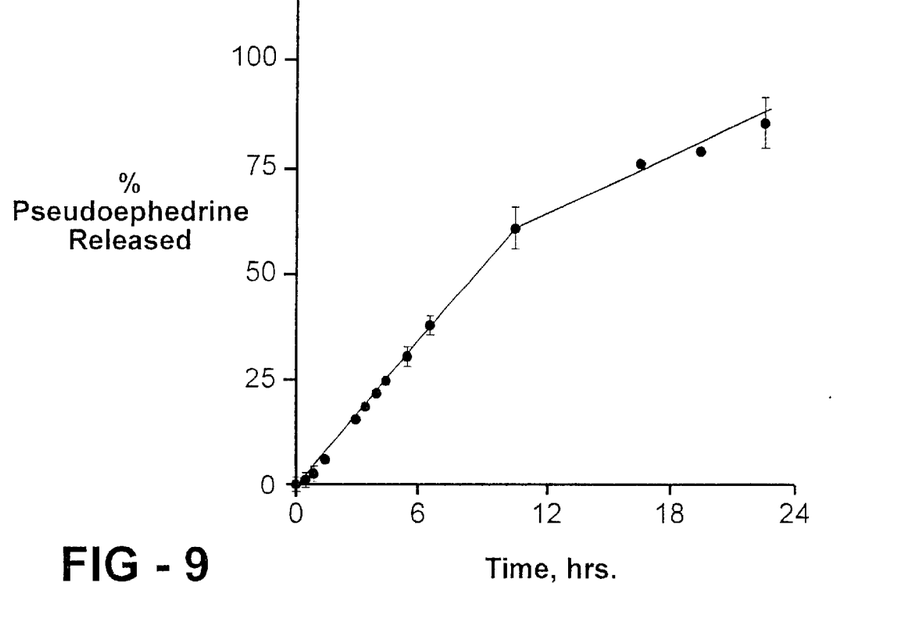
FIG. 9 is a graph illustrating release characteristics of the present invention.
Figure 10:
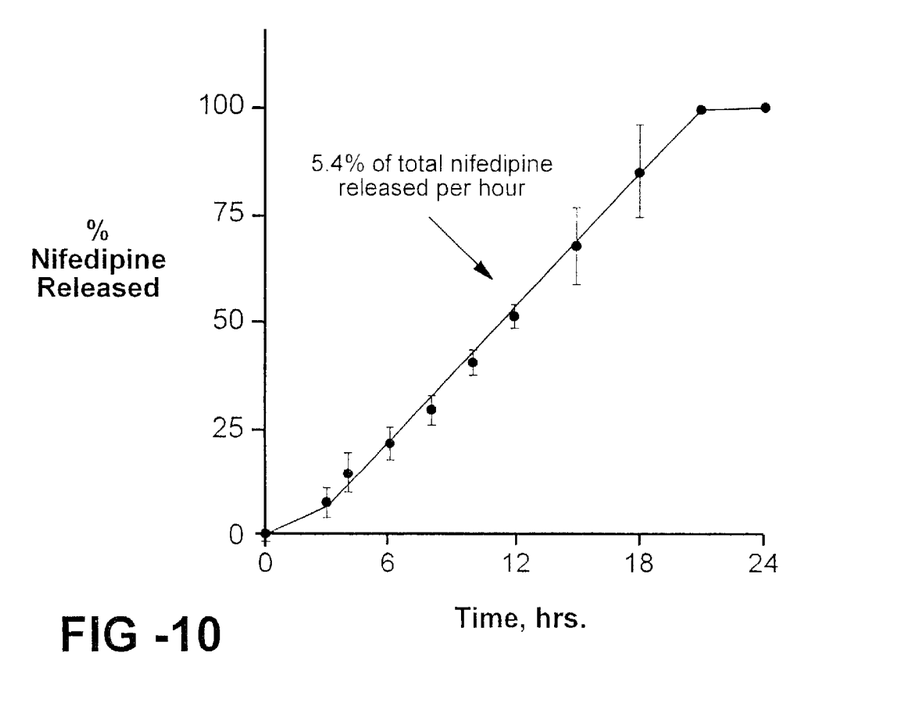
FIG. 10 is a graph illustrating release characteristics of the present invention.

FIG. 9 shows the sustained release of pseudoephedrine, a water soluble drug, formulated according to the present invention (mean ± standard error of the mean, n=3).

Example 3

Nifedipine

Nifedipine, a water insoluble drug, is the active drug ingredient in the formulations shown in Table 2.

TABLE 2

| LOT | INGREDIENT | PERCENT WEIGHT/WEIGHT (Total WEIGHT = 200 milligrams) |
|---|---|---|
| 1102-10B | nifedipine | 15.0 |
| | hydroxypropylcellulose | 83.0 |
| | carbomer | 0.0 |
| | magnesium stearate | 2.0 |
| | lactose | 0.0 |
| 1102-10C | nifedipine | 15.0 |
| | hydroxypropylcellulose | 49.0 |
| | carbomer | 26.0 |
| | magnesium stearate | 1.0 |
| | lactose | 9.0 |
| 1102-11B | nifedipine | 15.0 |
| | hydroxypropylcellulose | 0.0 |
| | carbomer | 15.0 |
| | magnesium stearate | 2.0 |
| | lactose | 68.0 |

Figure 12:
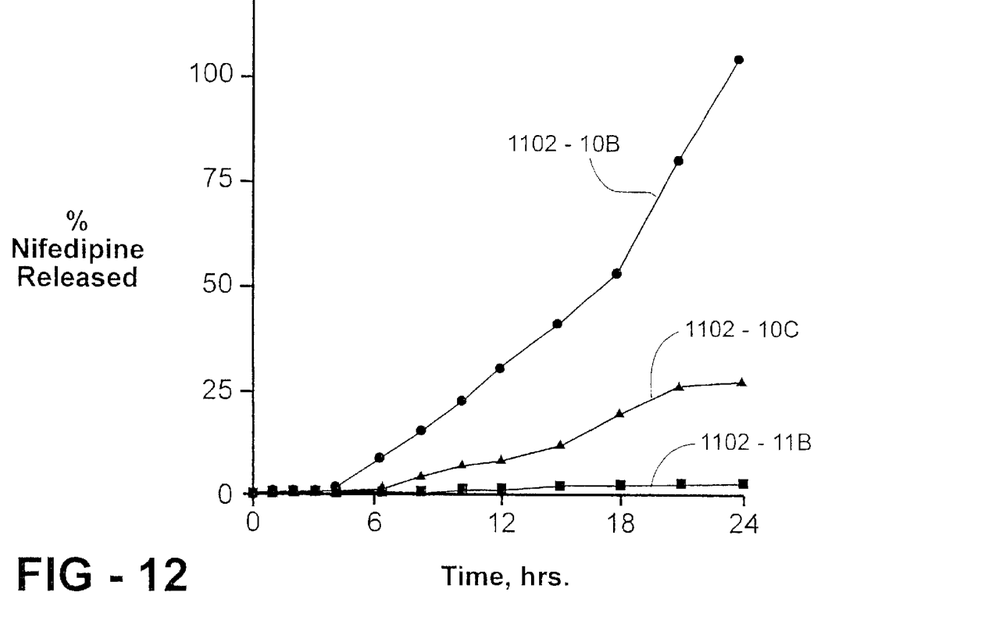
FIG. 12 is a graph illustrating release characteristics of the present invention.

FIG. 9 shows sustained release of nifedipine formulated according to the present invention (mean ± standard error of the mean, n=3). This formulation allows release of about 5.4% of total nifedipine per hour. FIG. 12 shows release rates of nifedipine differ according to the formulations of Table 2.

Example 4

Figure 11:
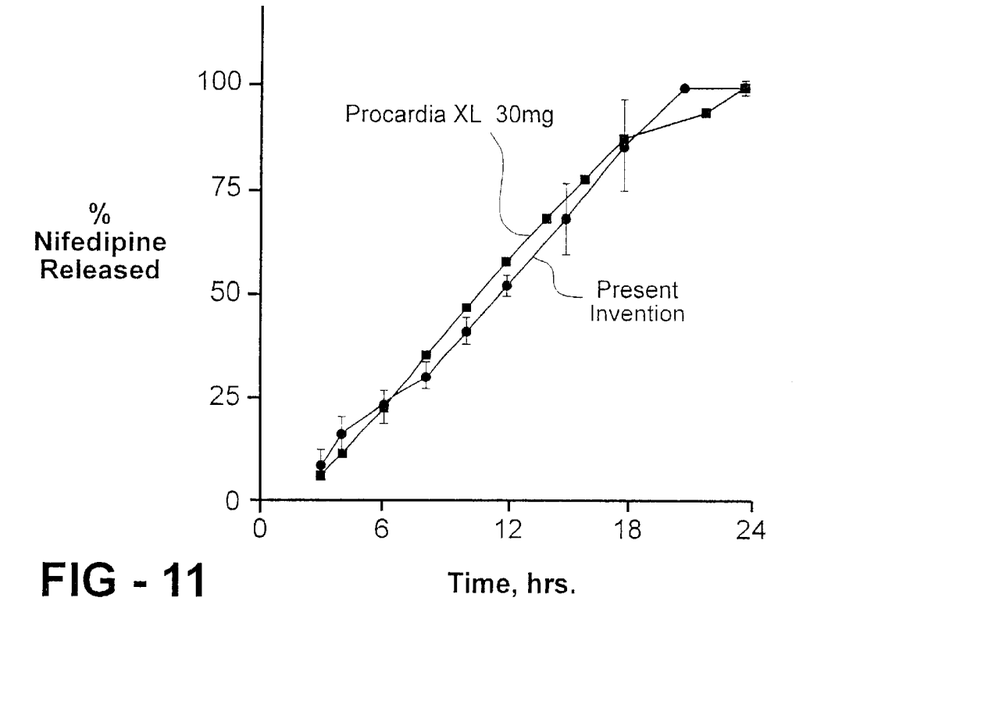
FIG. 11 is a graph illustrating release characteristics of the present invention.

FIG. 11 shows the release profile of nifedipine formulated according to the present invention to approximately match the release profile of a commercial sustained release formulation of nifedipine, Procardia XL® (mean ± standard error of the mean, n=3). Plotted values are the zero-order release rate portion of the dissolution profile.

Example 5

Figure 13:
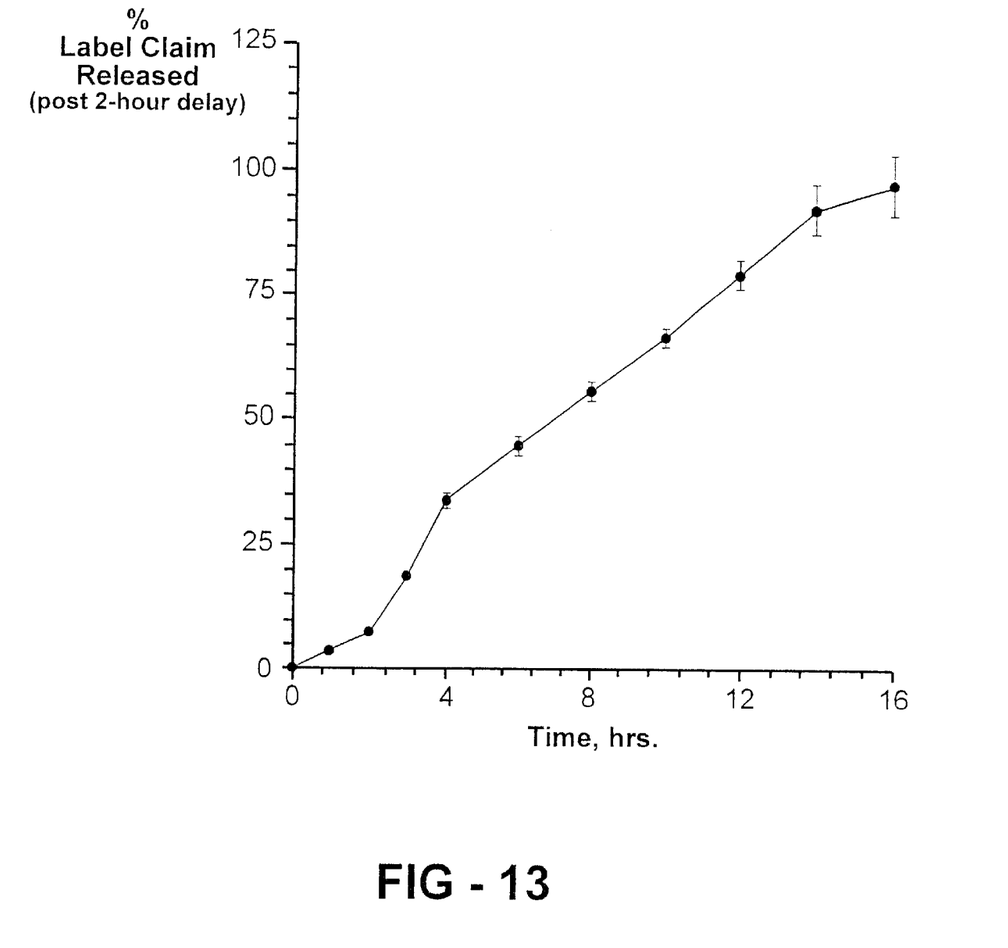
FIG. 13 is a graph illustrating release characteristics of the present invention.

An oral hypoglycemic agent, glipizide, is incorporated into the formulated, coated capsule body of the drug delivery system of the present invention. A dissolution experiment is performed using a Vankel USP dissolution apparatus maintained at 37° C. and a paddle speed of 50 rpm. The dissolution medium used is 50 mM phosphate buffer, pH 7.5. FIG. 13 shows a graph of the release over time.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A drug delivery system comprising:
   (a) a therapeutic amount of a pharmaceutical agent;
   (b) a container having (i) at least one aperture and (ii) a wall having an inside and an outside;
   (c) an excipient formulation disposed in said container regulating a diffusional boundary for said pharmaceutical agent, wherein the diffusional boundary layer is confined within said container for a period of time to allow drug delivery to a desired location and continuously releasing said pharmaceutical agent upon solvation at a rate of less than one-fifth of the initial release of said pharmaceutical agent in an uncoated form, the excipient formulation comprising a release control agent and an ingredient selected from the group consisting of: a lubricating agent, a filling agent and a mixture thereof, the ratio of the release control agent to the ingredient ranging from 0.2 to 170; and
   (d) a cover layer adhered to the wall, wherein at least one of the container or the cover layer is semi-permeable to said pharmaceutical agent.

2. The drug delivery system of claim 1 further comprising an aperture cover that is removable to expose the at least one aperture after a preselected length of time.

3. The drug delivery system of claim 1 wherein said container comprises a biocompatible polymer.

4. The drug delivery system of claim 1 wherein said container is selected from the group consisting of: hard gelatin, soft gelatin, hydroxypropylmethylcellulose and starch.

5. The drug delivery system of claim 1 wherein the pharmaceutical agent is selected from the group consisting of: organic, inorganic and organometallic.

6. The drug delivery system of claim 1 wherein the pharmaceutical agent has a molecular weight in the range of about 50 to about 10,000,000.

7. The drug delivery system of claim 1 wherein the pharmaceutical agent is selected from the group consisting of: an analgesic, an anesthetic, an anthelminthic, an antiallergic, an antiarrhythmic, an anti-asthmatic, an antibiotic, an anticonvulsant, an antidepressant, an antidiabetic, an antifungal, an antihypertensive, an anti-inflammatory agent, anti-migraine, an antineoplastic, an antiparasitic, an antitumor agent, an anti-ulcer agent, an antiviral, an anxiolytic, a bronchodilator, a cough or cold agent, a cytostatic, a hypnotic, a hypoglycemic, a metastasis inhibitor, a muscle relaxant, a neoplastic, a sedative and a tranquilizer compound.

8. The drug delivery system of claim 1 wherein the pharmaceutical agent is pseudoephedrine.

9. The drug delivery system of claim 1 wherein the pharmaceutical agent is nifedipine.

10. The drug delivery system of claim 1 wherein the pharmaceutical agent is acetominophen.

11. The drug delivery system of claim 1 wherein the pharmaceutical agent is glipizide.

12. The drug delivery system of claim 1 wherein said formulation remains disposed in said container when hydrated for a time effective to regulate release of said pharmaceutical agent.

13. The drug delivery system of claim 1 wherein said formulation comprises at least one ingredient selected from the group consisting of: a release control component, a lubricating agent and a filling agent.

14. The drug delivery system of claim 13 comprising at least one ingredient selected from the group consisting of: hydroxyalkylcellulose, carbomer, magnesium stearate and a saccharide.

15. The drug delivery system of claim 14 wherein the hydroxyalkylcellulose is present in amounts from about 0 to about 85% weight/weight, the carbomer is present in amounts from about 0 to about 30% weight/weight, the magnesium stearate is present in amounts from about 0.5 to about 3% weight/weight and the saccharide is present in amounts from about 0 to about 70% weight/weight.

16. The drug delivery system of claim 1 wherein said cover layer allows the inward passage of water.

17. The drug delivery system of claim 1 wherein said cover layer comprises a cellulose acetate material selected from the group consisting of: cellulose acetate butyrate, cellulose derivates and polyurethane.

18. The drug delivery system of claim 1 wherein said cover layer adheres to the outside of the wall.

19. The drug delivery system of claim 1 wherein said cover layer adheres to the inside of the wall.

20. The drug delivery system of claim 1 wherein said cover layer adheres to the inside and the outside of the wall.

21. A process for drug delivery comprising the step of administering to an individual a drug delivery device comprising:
   (a) a therapeutic amount of a pharmaceutical agent;
   (b) a container having (i) at least one aperture and (ii) a wall having an inside and an outside;
   (c) an excipient formulation disposed in said container regulating a diffusional boundary for said pharmaceutical agent, wherein the diffusional boundary layer is confined within said container for a period of time to allow drug delivery to a desired location and continuously releasing said pharmaceutical agent upon solvation at a rate of less than one-fifth of the initial release of said pharmaceutical agent in an uncoated form, the excipient formulation comprising a release control agent and an ingredient selected from the group consisting of: a lubricating agent, a filling agent and a mixture thereof, the ratio of the release control agent to the ingredient ranging from 0.2 to 170; and (d) a cover layer adhered to the wall, wherein at least one of the container or the cover layer is semi-permeable to said pharmaceutical agent.

22. The process for drug delivery of claim 21 further comprising an aperture cover that is removable to expose the at least one aperture after a preselected length of time.

23. The process for drug delivery of claim 21 wherein said container comprises a biocompatible polymer.

24. The process for drug delivery of claim 21 wherein said container is selected from the group consisting of: hard gelatin, soft gelatin, hydroxypropylmethylcellulose and starch.

25. The process for drug delivery of claim 21 wherein the pharmaceutical agent is selected from the group consisting of: organic, inorganic and organometallic.

26. The process for drug delivery of claim 21 wherein the pharmaceutical agent has a molecular weight in the range of about 50 to about 1,000,000.

27. The process for drug delivery of claim 21 wherein the pharmaceutical agent is selected from the group consisting of: antihypertensives, antiallergics, anxiolytics, bronchodilators, anti-asthmatics, hypoglycemics, cough or cold agents, neoplastics, anti-ulcer agents, antineoplastics, antitumor agents, hypnotics, sedatives, tranquilizers, anesthetics, muscle relaxants, anticonvulsants, antidepressants, antibiotics, analgesics, antivirals, anti-inflammatory agents, antidiabetics, anti-migraines, cytostatics and metastasis inhibitors, antiarrhythmics, antibiotics, antifungals, antivirals, anthelminthics, and antiparasitic compounds.

28. The process for drug delivery of claim 21 wherein the pharmaceutical agent is pseudoephedrine.

29. The process for drug delivery of claim 21 wherein the pharmaceutical agent is nifedipine.

30. The process for drug delivery of claim 21 wherein the pharmaceutical agent is acetominophen.

31. The drug delivery system of claim 21 wherein the pharmaceutical agent is glipizide.

32. The process for drug delivery of claim 21 wherein said formulation remains disposed in said container when hydrated for a time effective to regulate release of said pharmaceutical agent.

33. The process for drug delivery of claim 21 wherein the formulation comprises at least one ingredient selected from the group consisting of: a release control component, a lubricating agent and a filling agent.

34. The process for drug delivery of claim 21 comprising at least one ingredient selected from the group consisting of: hydroxyalkylcellulose, carbomer, magnesium stearate and a saccharide.

35. The process for drug delivery of claim 32 wherein the hydroxyalkylcellulose is hydroxypropylmethylcellulose that is present in amounts from about 0 to about 85% weight/weight, the carbomer is present in amounts from about 0 to about 30% weight/weight, the magnesium stearate is present in amounts from about 0.5 to about 3% weight/weight and the saccharide is present in amounts from about 0 to about 70% weight/weight.

36. The process for drug delivery of claim 21 wherein said cover layer allows the inward passage of water.

37. The process for drug delivery of claim 21 wherein said cover layer adheres to the outside of the wall.

38. The process for drug delivery of claim 21 wherein said cover layer adheres to the inside of the wall.

39. The process for drug delivery of claim 21 wherein said cover layer adheres to the inside and the outside of the wall.

40. The process for drug delivery of claim 21 wherein said cover layer comprises a material selected from the group consisting of: cellulose acetate butyrate, cellulose derivatives and polyurethane.

41. The process for drug delivery of claim 21 wherein the individual is selected from the group consisting of: sheep, cattle, horses, goats, pigs, chickens, dogs and cats.

42. The process for drug delivery of claim 21 wherein the individual is human.

43. The process for drug delivery of claim 21 wherein the administration is by a route selected from the group consisting of: oral, rectal, parenteral, intravenous, intramuscular, subcutaneous, intracisternal, intravaginal, intraperitonal, intravesical, intraventricular, intracranial, and intrathecal.

* * * * *